United States Patent
Lienard et al.

(10) Patent No.: US 6,831,644 B2
(45) Date of Patent: Dec. 14, 2004

(54) METHOD AND DEVICE FOR DISPLAYING THE DEPLOYMENT OF AN ENDOVASCULAR PROSTHESIS

(75) Inventors: Jean Lienard, Igny (FR); Francisco Sureda, Chatenay Malabry (FR); Regis Vaillant, Villebon sur Yvette (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 219 days.

(21) Appl. No.: 10/175,634

(22) Filed: Jun. 19, 2002

(65) Prior Publication Data

US 2003/0011600 A1 Jan. 16, 2003

(30) Foreign Application Priority Data

Jun. 29, 2001 (FR) .............................................. 01 08650

(51) Int. Cl.[7] .............................................. G06T 15/00
(52) U.S. Cl. ...................................................... 345/428
(58) Field of Search ................................ 345/419, 420, 345/426, 427, 428, 617, 660, 671; 600/423, 426; 378/98.2

(56) References Cited

U.S. PATENT DOCUMENTS

| | | | | |
|---|---|---|---|---|
| 5,431,162 A | * | 7/1995 | McArdle | 600/426 |
| 5,457,728 A | | 10/1995 | Whiting et al. | 378/98.2 |
| 6,280,385 B1 | * | 8/2001 | Melzer et al. | 600/423 |

FOREIGN PATENT DOCUMENTS

DE 19935916 3/2001

OTHER PUBLICATIONS

Watson et al., "What Does the Eye See Best", MacMillan Journals, Ltd, 1983.

Pattanaik et al, "A Multiscale Model of Adaptation and Spatial Vision for Realistic Image Display" Computer Graphic Proceedings, Annual Conference Series 1998, pp. 287–298.

Talukdar et al, "Modeling and Optimization of Rotational C–Arm Stereo Scopic X–Ray Angiography", IEEE Transactions on Medical Imaging, vol. 18, No. 17, Jul. 1999, pp 604–616.

* cited by examiner

Primary Examiner—Almis R. Jankus
(74) Attorney, Agent, or Firm—Jay L. Chaskin; Cantor Colburn LLP

(57) ABSTRACT

An element is dissolved displayed having a periodic structure, such as a stent, images of which are acquired by means of a radiography machine of the type comprising an X-ray source and an image detector and an image display placed opposite the source. The images obtained are displayed with an overall magnification of:

$$\frac{f_S}{f_{CSF}} \times ESD \times \frac{\pi}{180},$$

where $f_S$ is the fundamental frequency, being the inverse of the spatial period of the stent in pairs of lines per millimeter, where $f_{CSF}$ is the spatial frequency corresponding to the contrast sensitivity maximum for the human eye in cycles per degree; and where ESD is the expected distance in millimeters between the images displayed and an observer viewing these images.

30 Claims, 3 Drawing Sheets

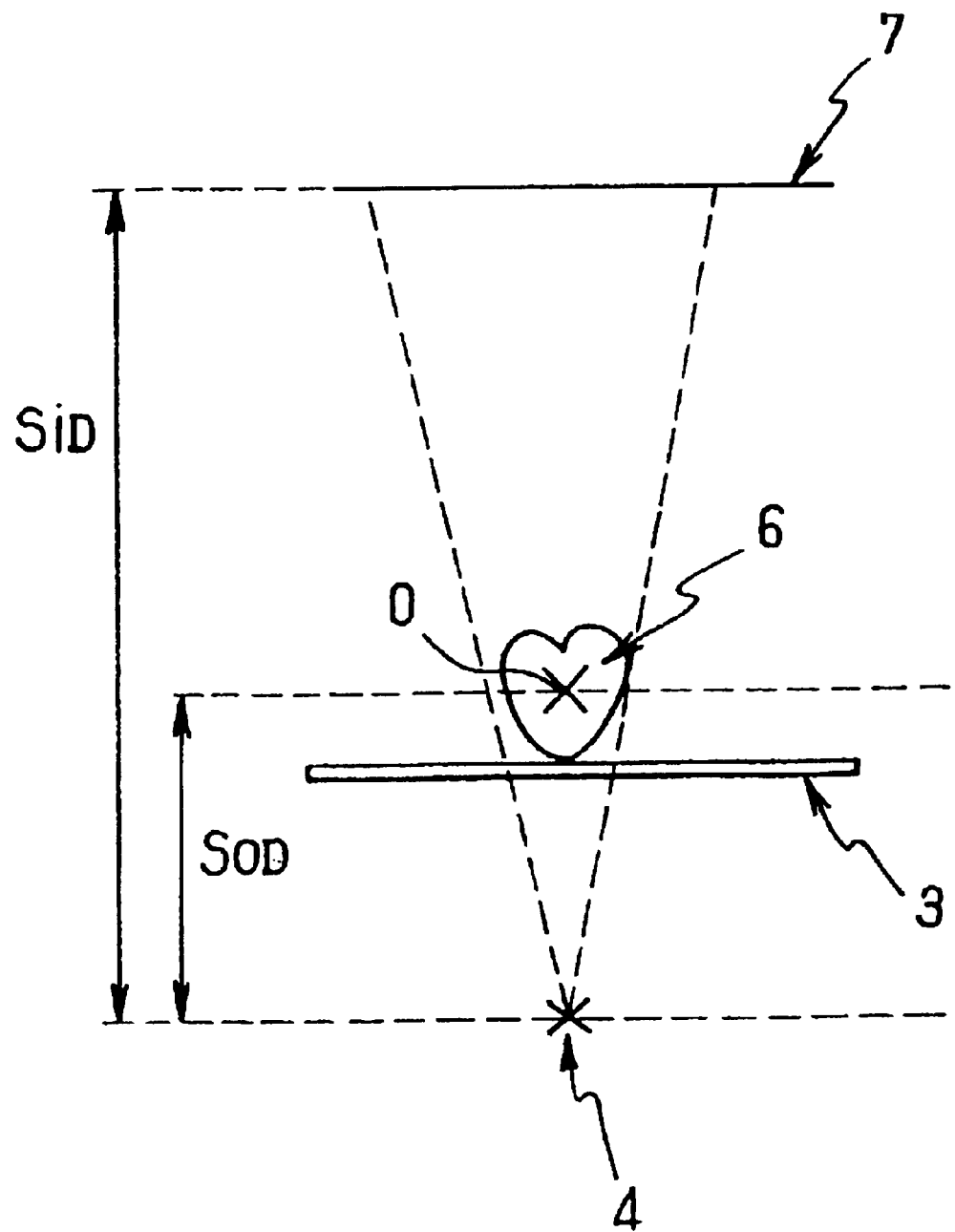
FIG_2

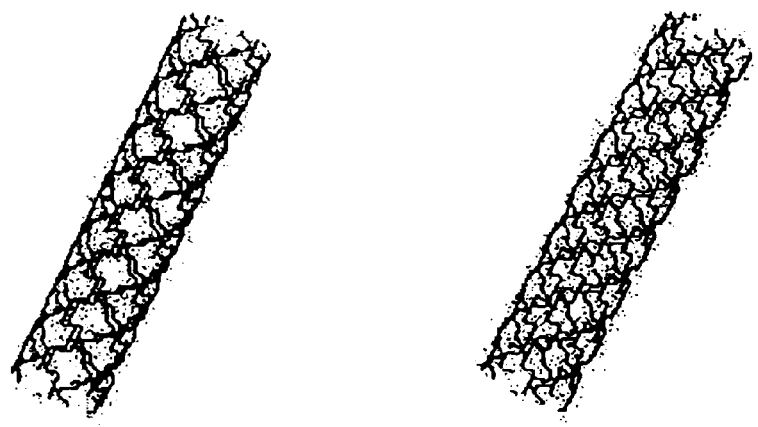
FIG_4
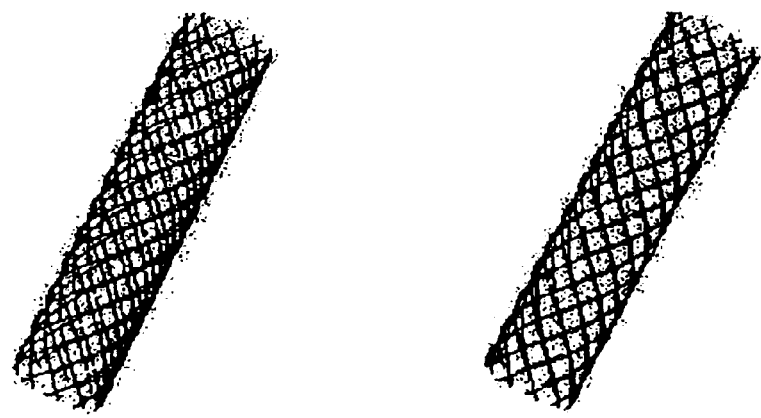
FIG_5

METHOD AND DEVICE FOR DISPLAYING THE DEPLOYMENT OF AN ENDOVASCULAR PROSTHESIS

CROSS REFERENCE TO RELATED APPLICATIONS

This application claims the benefit of a priority under 35 USC 119 to French Patent Application No. 01 08650 filed Jun. 29, 2001, the entire contents of which are incorporated by reference.

BACKGROUND OF THE INVENTION

The invention relates to stereoscopic imaging methods in radiology. It relates in particular to the displaying of an endovascular prosthesis, generally called a stent, in a vessel.

Stents are prostheses which are widely used to enhance or increase the diameter of a vessel or an artery. These stents are generally cylindrical elements having a periodic lattice structure which allows them to be deployed radially. During a surgical procedure comprising implanting a stent in a vessel, the operator must ensure that the stent has been positioned and deployed satisfactorily. This verification is essential in order to avoid any subsequent risk of new stenosis, that is, a new retraction of the vessel walls. For this purpose, the operator performs an X-ray angiography to display the patient's vessel or artery into which the stent has been implanted. The disadvantage of this technique is that the images are obtained by projection, which therefore gives only a two-dimensional view of the stent. The operator may display the vessel using intravascular ultrasound (IVUS) techniques to obtain, for example, cross-sectional images along the axis of the stent. However, these techniques require the insertion into the vessel of an ultrasound probe carried at the end of a specific catheter, the catheter being connected to an IVUS imaging apparatus.

Furthermore, stents are particularly difficult to display on X-ray angiographic images because of their small thickness. This low opacity is generally due to the low density of the material of which they are made and to their geometrical configuration in the form of a lattice, which has a high proportion of empty spaces.

BRIEF DESCRIPTION OF THE INVENTION

An embodiment of the invention provides a method for displaying an element having a periodic structure, such as a stent, images of which are acquired by means of a radiography machine of the type comprising means for providing a radiation source, such as an X-ray source and means for detection placed opposite the source, wherein the images obtained are displayed with an overall magnification of:

$$\frac{f_S}{f_{CSF}} \times ESD \times \frac{\pi}{180},$$

where $f_S$ is the fundamental frequency, being the inverse of the spatial period of the stent in pairs of lines per millimeter; where $f_{CSF}$ is a spatial frequency corresponding to the contrast sensitivity maximum for the human eye in cycles per degree; and
where ESD is the expected distance in millimeters between means for displaying images and an observer viewing these images.

An embodiment of the invention is a system for displaying an element having a periodic structure, such as a stent, comprising means for image acquisition in a radiography machine, the machine comprising means for providing a source of radiation and means for detection placed opposite the source, means for display, and means for processing for implementing the method.

BRIEF DESCRIPTION OF THE DRAWINGS

The embodiments of the invention will be better understood from the following description, which is purely illustrative but non-limiting, and read in conjunction with the appended drawings in which:

FIG. 2 is a diagram representative of the device employed for obtaining a stereoscopic image;

FIGS. 4 and 5 are examples of stereoscopic images of stents obtained.

DETAILED DESCRIPTION OF THE INVENTION

Advantageously, in particular for displaying the images with a magnification, a numerical zoom is applied to the obtained images intended to be displayed, the zoom being equal to:

$$M_Z = \frac{\pi \times f_S \times ESD \times FOV \times SOD}{180 \times f_{CSF} \times FOD \times SID}$$

where FOV denotes the field of projection of the image on the means for detection, SOD is the distance between the source and the periodic element to be displayed, FOD denotes the field of display of the image on the means for display and SID is the distance between the source and the means for detection.

Advantageously, embodiments of the invention improves the conditions under which the stent is viewed, using conventional X-ray imaging devices.

Advantageously, embodiments of the invention obtain the optimum conditions for displaying the stent, taking into account the characteristics of the human eye and the characteristics of the image acquisition device.

In an embodiment of implementing the method frequency components corresponding to spatial frequencies which are a multiple of the fundamental frequency $f_S$ are intensified on the images obtained. In this way, the contrast of the stent on the displayed images is improved, bringing out its periodic structure.

Advantageously, several images may be displayed in parallel on one display device. More specifically, the radiography device can perform the acquisition of at least two images focused on the element and display them in pairs on a stereoscopic display device. Stereoscopic display provides the operator with a view of the element in relief and allows a better assessment of its deployment in the patient's vein or artery. In particular, since the source and the means for detection are mounted on an arch which can be rotated on itself about at least one axis, at least two series of image acquisitions corresponding to two different angular positions of the arch are performed, the angle through which the latter is rotated between these two series of acquisitions being about 1.5 to 2 degrees.

The apparent frequency $f_{CSF}$ of the structure of the element displayed is preferably chosen between 3 and 8 cycles per degree of viewing angle. These frequencies correspond to a range within which a frequency corresponding to the maximum of the human eye's contrast sensitivity function CSF generally lies.

It is also possible to employ a technique of locating and tracking the displayed element so as to stabilize its image on the display device according to its location.

Figure 1:
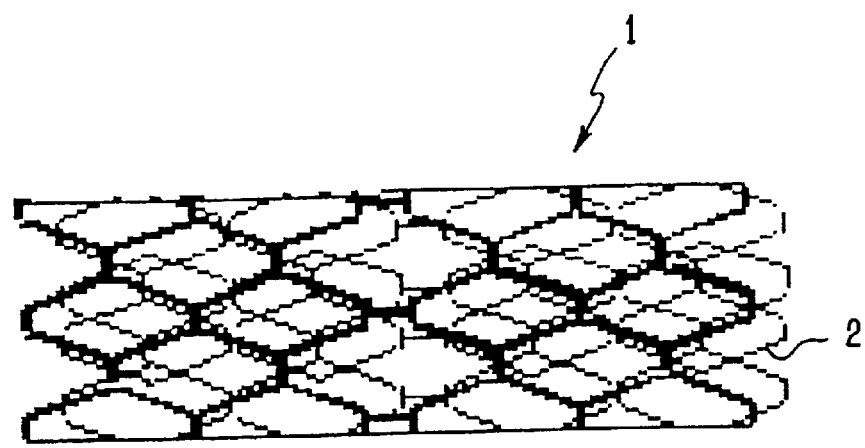
FIG. 1 shows an example of a periodic stent structure.

FIG. 1 shows an example of a stent structure. In this figure, a stent 1 comprises wire elements 2 having a thickness of about 0.10 mm, these being combined so as to create a generally cylindrical lattice structure. This specific structure allows the stent 1 to be expanded or retracted radially. In cardiology, stents have diameters of about 2 to 4 mm and lengths of between 10 and 40 mm. Once the stent has been deployed, it forms a periodic structure whose period T is approximately 1.5 mm.

Conventional image analysis techniques comprises decomposing the images into a spectrum of spatial frequencies. These spatial frequencies are frequencies representative of the number of successive light and dark lines (pairs of lines) per millimeter in the image. It has been found, on the one hand, that the frequency spectrum of the geometrical configuration of a stent exhibits amplitude peaks at the spatial frequencies which are multiples of the fundamental frequency $f_S$ defined by:

$$f_S = \frac{1}{T}.$$

In the case of the stent shown in FIG. 1, $f_S$ is 0.7 pairs of lines (pl) per millimeter.

On the other hand, it has been shown that the human eye's sensitivity to the sinusoidal patterns of a small grid of low contrast has a response of the type of that of a band-pass filter. This response is given by a contrast sensitivity function (CSF). For example, for an intensity of illumination of the order of 10 to 100 candela (cd) per square meter, this function has a maximum in the case of grids having frequencies of between 3 and 8 cycles per degree of viewing angle. Watson et al. ("What does the eye see best?", by A. B. Watson, H. B. Barlow and J. G. Robson, Macmillan Journals Ltd., 1983) estimate that the optimum frequency detected by the eye is between 6 and 8 cycles per degree of viewing angle for an illumination of 340 cd/m².

Taking into account the above observations, it may be desired to improve the display of the stent by the operator in the following manner:

1) by displaying the images of the stent at the spatial frequency corresponding to the maximum of the CSF;

2) by intensifying the frequency components of the images corresponding to the spatial frequencies which are multiples of the fundamental frequency $f_S$ so as to obtain the optimum contrast of the images;

3) by displaying the images in stereoscopic vision on a specific screen.

Figure 3:
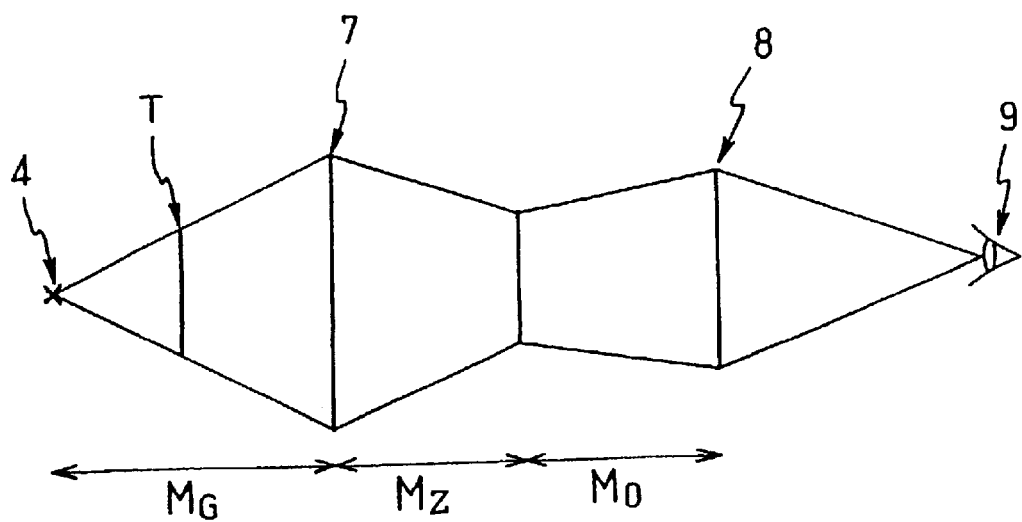
FIG. 3 shows the various enlargement ratios involved in obtaining an image corresponding to the optimum sensitivity of the eye.

Firstly, it may be desired to enlarge the image displayed, so that the stent can be displayed at the frequency corresponding to the maximum of the CSF. FIG. 2 shows schematically the image capture device. This device comprises a table 3 on which the patient is placed, an X-ray source 4, which illuminates that part of the patient's body in which the stent 1 has been placed (for example the heart 6), and a detector 7 on which the image of the patient is projected. FIG. 3 shows three enlargement ratios employed:

(1) a geometric enlargement MG due to the projection performed by the image capture device;

(2) an optical enlargement MO due to the display on the screen; and (3) an enlargement MZ corresponding to the zoom on the displayed images.

The enlargement $M_G$ is the ratio of the distance SID between the source 4 and the plane of projection 7 of the image capture device to the distance SOD between the source 4 and the patient's heart 6, namely:

$$M_G = \frac{SID}{SOD}$$

The optical enlargement $M_O$ is the ratio of the field of display FOD of the image, that is to say the size of the screen 8, to the field of projection FOV of the image, that is to say the size of the detector 7, namely:

$$M_O = \frac{FOD}{FOV}.$$

The total enlargement $M_G \times M_O \times M_Z$ should allow the eye 9 of the operator viewing the image at a distance ESD from the screen 8 to perceive the structure of the stent at the spatial frequency $f_{CSF}$ corresponding to the maximum of the CSF. This corresponds to the following condition:

$$\frac{M_G \times M_O \times M_Z}{f_S} = \frac{ESD \times \pi}{f_{CSF} \times 180}.$$

From this equation, it is possible to deduce the enlargement $M_Z$ allowing the operator the best display of the stent, namely:

$$M_Z = \frac{\pi \times f_S \times ESD \times FOV \times SOD}{180 \times f_{CSF} \times FOD \times SID}.$$

For example, a mean value, regarded as optimum, of 4 cycles per degree may be taken for angiographic images displayed on a monitor operating with approximately 30 cd/m², that is:

$f_{CSF}$=4 pl/degree.

In the case of the other variables, the following values may also be taken:

FOV=200 mm;
SOD=720 mm;
ESD=500 mm;
FOD=300 mm;
SID=1 000 mm;
$f_S$=0.7 pl/mm.

An enlargement $M_Z$=0.73 is obtained. By applying this enlargement, the stent may be more easily viewed by the operator. The operator may thus check that the stent 1 has been positioned and deployed satisfactorily.

Secondly, the intensity of the frequency components of the images obtained, corresponding to the spatial frequencies which are multiples of the fundamental frequency $f_S$, which was about 0.7 pl/mm in the case of the stent shown in FIG. 1, is increased. This condition may be fulfilled by using a filter whose response corresponds to multiple passbands centred on the multiples of $f_S/M_G$. This improves the contrast of the stent on the displayed images, bringing out its structure.

Thirdly, it may be desired to view a pair of images centered on the stent so as to display them in stereoscopic vision on a specific screen. In FIG. 2, the table 3 has been placed so that the patient's heart 6 lies at the isocentre O of the arch supporting the image acquisition device. In this way, the distance SOD between the source 4 and the patient's heart 6 remains constant for each image taken. Once the stent has been positioned and deployed in the internal space of the vessel, the acquisition of a first series of images is performed without injection. Owing to the patient's position on the operating table, this acquisition is centered on the stent. This acquisition is performed with the shortest possible distance SID between the source 4 and the plane of projection 7 of the image capture device, according to the recommendations of Talukdar et al. ("*Modeling and Optimization of Rotational C-Arm Stereoscopic X-ray Angiography*" by A. S. Talukdar and D. L. Wilson, IEEE Transactions on Medical Imaging, Vol. 18, No. 7, Jul. 1999, pages 604 to 616). The acquisition time must be at least equal to one cardiac cycle. The electrocardiogram is recorded during this acquisition. Next, the arch is rotated through an angle α so as to perform a second series of acquisitions under the same conditions as the previous acquisition (the same field FOV and the same distance SID). The duration of this second series of acquisitions is at least that of one cardiac cycle. The two series of acquisitions are performed at two viewing points offset by an angle α. These two series of acquisitions constitute a series of stereoscopic views of the stent. To obtain optimum stereoscopic viewing, for both convergence and accommodation, the angle α must remain less than 2 degrees. A number of planes corresponding to a cardiac cycle are selected from each of the two series of images acquired, the first plane selected being chosen at the moment of the end of the diastolic period of the cardiac cycle.

These two selections constitute stereoscopic views which can be displayed side by side on the same screen or on a specific stereoscopic viewing device. The images may be enlarged by a factor $M_Z$, as calculated above, so that the apparent period of the geometrical structure of the stent corresponds to the maximum of the CSF.

FIG. 4 is an example of a stereoscopic image of a synthetic stent of the Palmaz-Schatz type, displayed in two positions of the arch of the image capture device which are offset by an angle α of 10 degrees.

FIG. 5 is another example of a stereoscopic image of a synthetic stent, of the Wallstent type, displayed in two positions of the arch of the image capture device offset by an angle α of 10 degrees.

In addition, to further improve the quality of the display, it is possible to apply, in combination with the display method described above, a technique of tracking the blood vessel so as to stabilize the stent on the screen. U.S. Pat. No. 5,457,728 describes a method of tracking and stabilizing a coronary artery in angiographic sequences.

Of course, the display method of the invention can be applied whenever it is desired to display an element whose structure comprises a geometrical pattern repeated with a given frequency.

Various modifications in structure and/or steps and/or function may be made by one skilled in the art without departing from the scope and extent of the invention as recited in the claims.

What is claimed is:

1. A method for displaying an element having a periodic structure, images of which are acquired by means of a radiography device of the type comprising means for providing a source of radiation and means for detection and display placed opposite the source, comprising:

displaying images obtained with an overall magnification of:

$$\frac{f_S}{f_{CSF}} \times ESD \times \frac{\pi}{180},$$

where $f_S$ is the fundamental frequency, being the inverse of the spatial period of the element in pairs of lines per millimeter;

where $f_{CSF}$ is a spatial frequency corresponding to the contrast sensitivity maximum for the human eye in cycles per degree; and where ESD is the expected distance in millimeters between the means for displaying the images and an observer viewing these images.

2. The method according to claim 1 comprising:

displaying the images with such a magnification, a numerical zoom is applied to the obtained images intended to be displayed, the zoom being equal to:

$$M_Z = \frac{\pi \times f_S \times ESD \times FOV \times SOD}{180 \times f_{CSF} \times FOD \times SID}$$

where FOV denotes the field of projection of the image on a means for detection, SOD is the distance between the source and the periodic element to be displayed, FOD denotes the field of display of the image on the means for display and SID is the distance between the source and the means for detection.

3. The method according to claim 2 wherein frequency components corresponding to spatial frequencies which are a multiple of the fundamental frequency $f_S$ are intensified on the images obtained.

4. The method according to claim 2 comprising:

performing the acquisition of at least two images focused on the element and displaying the images in pairs on a stereoscopic display.

5. The method according to claim 4 wherein the source and the means for detection are mounted on an arch which can be rotated on itself about at least one axis, at least two series of image acquisitions corresponding to two different angular positions of the arch are performed, the angle through which the latter is rotated between these two series of acquisitions being about 1.5 to 2 degrees.

6. The method according to claim 2 wherein $f_{CSF}$ is chosen between 3 and 8 cycles per degree of viewing angle.

7. The method according to claim 2 wherein during the acquisition step, a technique is employed whereby the element is located and tracked and the image is stabilized according to its location.

8. The method according to claim 1 wherein frequency components corresponding to spatial frequencies which are a multiple of the fundamental frequency $f_S$ are intensified on the images obtained.

9. The method according to claim 8 comprising:

performing the acquisition of at least two images focused on the element and displaying the images in pairs on a stereoscopic display.

10. The method according to claim 9 wherein the source and the means for detection are mounted on an arch which can be rotated on itself about at least one axis, at least two series of image acquisitions corresponding to two different angular positions of the arch are performed, the angle through which the latter is rotated between these two series of acquisitions being about 1.5 to 2 degrees.

11. The method according to claim 8 wherein $f_{CSF}$ is chosen between 3 and 8 cycles per degree of viewing angle.

12. The method according to claim 8 wherein during the acquisition step, a technique is employed whereby the element is located and tracked and the image is stabilized according to its location.

13. The method according to claim 1 comprising:

performing the acquisition of at least two images focused on the element and displaying the images in pairs on a stereoscopic display.

14. The method according to claim 13 wherein the source and the means for detection are mounted on an arch which can be rotated on itself about at least one axis, at least two series of image acquisitions corresponding to two different angular positions of the arch are performed, the angle through which the latter is rotated between these two series of acquisitions being about 1.5 to 2 degrees.

15. The method according to claim 14 wherein $f_{CSF}$ is chosen between 3 and 8 cycles per degree of viewing angle.

16. The method according to claim 14 wherein during the acquisition step, a technique is employed whereby the element is located and tracked and the image is stabilized according to its location.

17. The method according to claim 13 wherein $f_{CSF}$ is chosen between 3 and 8 cycles per degree of viewing angle.

18. The method according to claim 13 wherein during the acquisition step, a technique is employed whereby the element is located and tracked and the image is stabilized according to its location.

19. The method according to claim 1 wherein $f_{CSF}$ is chosen between 3 and 8 cycles per degree of viewing angle.

20. The method according to claim 19 wherein during the acquisition step, a technique is employed whereby the element is located and tracked and the image is stabilized according to its location.

21. The method according to claim 1 wherein during the acquisition step, a technique is employed whereby the element is located and tracked and the image is stabilized according to its location.

22. The method according to claim 1 wherein the element is a stent.

23. A radiography device for displaying an element having a periodic structure comprising:

(a) means for image acquisition;

(b) means for providing a source of radiation;

(c) means for detection;

(d) means for display; and (e) means for processing for displaying the images obtained with an overall magnification of:

$$\frac{f_S}{f_{CSF}} \times ESD \times \frac{\pi}{180},$$

where $f_S$ is the fundamental frequency, being the inverse of the spatial period of the element in pairs of lines per millimeter;

where $f_{CSF}$ is a spatial frequency corresponding to the contrast sensitivity maximum for the human eye in cycles per degree; and where ESD is the expected distance in millimeters between the means for displaying the images and an observer viewing these images.

24. The device according to claim 23 wherein the element is a stent.

25. The device according to claim 23 wherein the means for processing displays the image with such a magnification, a numerical zoom is applied to the obtained images intended to be displayed, the zoom being equal to:

$$M_Z = \frac{\pi \times f_S \times ESD \times FOV \times SOD}{180 \times f_{CSF} \times FOD \times SID}$$

where FOV denotes the field of projection of the image on the means for detection, SOD is the distance between the source and the periodic element to be displayed, FOD denotes the field of display of the image on the means for display and SID is the distance between the source and the means for detection.

26. The device according to claim 23 wherein the frequency components corresponding to spatial frequencies which are a multiple of the fundamental frequency $f_S$ are intensified on the images obtained.

27. The device according to claim 23 wherein the means for processing performs the acquisition of at least two images focused on element and displaying the images in pairs on a stereoscopic display.

28. The device according to claim 27 wherein the source and the means for detection are mounted on an arch which can be rotated on itself about at least one axis, at least two series of image acquisitions corresponding to two different angular positions of the arch are performed, the angle through which the latter is rotated between these two series of acquisitions being about 1.5 to 2 degrees.

29. The device according to claim 23 wherein $f_{CSF}$ is chosen between 3 and 8 cycles per degree of viewing angle.

30. The device according to claim 23 wherein the element is located and track and the image is stabilized according to its location.

* * * * *